United States Patent

Faiardi et al.

[11] Patent Number: 5,510,469
[45] Date of Patent: Apr. 23, 1996

[54] 2-ACYLOXY-4-MORPHOLINYL ANTHRACYCLINES

[75] Inventors: Daniela Faiardi, Pavia; Alberto Bargiotti; Antonino Suarato, both of Milan, all of Italy

[73] Assignee: Farmitalia Carlo Erbq S.R.L., Milan, Italy

[21] Appl. No.: 987,281

[22] PCT Filed: Aug. 8, 1991

[86] PCT No.: PCT/EP91/01506

§ 371 Date: May 12, 1993

§ 102(e) Date: May 12, 1993

[87] PCT Pub. No.: WO92/04362

PCT Pub. Date: Mar. 19, 1992

[30] Foreign Application Priority Data

Sep. 12, 1990 [GB] United Kingdom ............... 9019934.0

[51] Int. Cl.$^6$ ..................................... C07H 15/24
[52] U.S. Cl. .................... 536/6.4; 536/17.4; 536/18.5; 536/18.6
[58] Field of Search ................. 536/6.4, 18.5, 536/18.6, 17.4, 17.4; 514/34

[56] References Cited

U.S. PATENT DOCUMENTS

| | | | |
|---|---|---|---|
| 4,438,105 | 3/1984 | Suarato et al. | 514/34 |
| 4,672,057 | 6/1987 | Bargiotti et al. | 514/34 |
| 4,684,629 | 8/1987 | Bargiotti et al. | 514/34 |
| 4,710,564 | 12/1987 | Otake et al. | 536/6.4 |
| 4,772,688 | 9/1988 | Morton et al. | 536/6.4 |
| 4,839,346 | 6/1989 | Bargiotti et al. | 514/34 |
| 4,891,360 | 1/1990 | Angelucci et al. | 514/34 |
| 4,959,460 | 12/1990 | Nakajima et al. | 536/6.4 |
| 4,985,548 | 1/1991 | Caruso et al. | 536/6.4 |
| 4,987,126 | 1/1991 | Bargiotti et al. | 514/34 |
| 5,045,534 | 9/1991 | Bargiotti et al. | 514/34 |
| 5,138,044 | 8/1992 | Davgupta | 536/18.5 |
| 5,218,130 | 6/1993 | Cabri et al. | 552/201 |

FOREIGN PATENT DOCUMENTS 2172594 12/1986 United Kingdom.

OTHER PUBLICATIONS

Chemical Abstracts, vol. 113, No. 19, Nov. 5, 1990, Columbus, Ohio, US; abstract No. 172649m, & JP,A, 0,269,494 (Kirin Brewery Co., Ltd.), Mar. 8, 1990.

*Primary Examiner*—Elli Peselev

[57] ABSTRACT

Anthracycline glycosides of formula 1:

wherein $R_1$ is hydrogen or methoxy group; $R_2$ is hydrogen or hydroxy; both $R_3$ and $R_4$ represent hydrogen or one of $R_3$ and $R_4$ is hydroxy and the other of $R_3$ and $R_4$ a represents hydrogen; $R_5$ represents hydrogen atom or an acyl residue—COX in which X is a $C_1$–$C_8$ linear or branched alkyl chain, an aryl, an aryl lower alkyl, or a 5- or 6-membered heteroaromatic group are anti-tumour agents.

2 Claims, No Drawings

2-ACYLOXY-4-MORPHOLINYL ANTHRACYCLINES

The invention relates to a new anthracycline glycosides, to processes for their preparation and to pharmaceutical compositions containing them.

A new class of anthracycline glycoside antibiotics in which the 3'-nitrogen atom of the sugar moiety is enclosed in a 4-morpholino ring bearing a hydroxy or acyloxy substituent at position C-2 have now been found. The present invention therefore provides an anthracycline glycoside of formula 1.

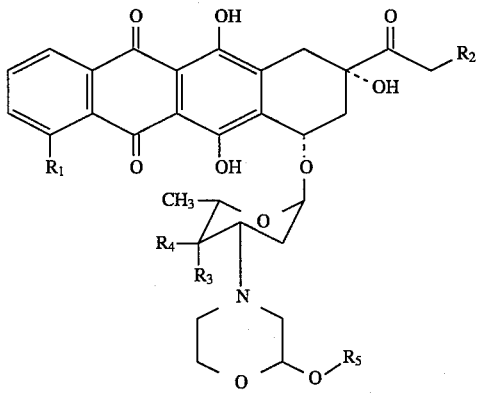

wherein $R_1$ is hydrogen or a methoxy group; $R_2$ is hydrogen or hydroxy; both $R_3$ and $R_4$ represent hydrogen or one of $R_3$ and $R_4$ is hydroxy and the other of $R_3$ and $R_4$ represents hydrogen; $R_5$ represents hydrogen atom or an acyl residue —COX in which X is a $C_1$–$C_8$ linear or branched alkyl, an aryl an aryl, (lower alkyl), or a 5- or 6- membered heteroaromatic group; or a pharmaceutically acceptable salt thereof.

In particular X may be a linear or branched alkyl group containing from 1 to 6 carbon atoms, for example 1 to 4 carbon atoms. X may in particular be methyl, ethyl, n-propyl, iso-propyl, n-butyl, iso-butyl or tert-butyl.

Alternatively X may be an aryl group such as a phenyl or naphthyl group, unsubstituted or substituted by 1 to 3 substituents each of which may independently be a linear or branched alkyl or alkoxy group of from 1 to 6 carbon atoms for example from 1 to 3 carbon atoms, a halogen atom or a nitro group.

If X represents an aryl (lower alkyl) group then the alkyl group may be linear or branched alkyl group and may contain up to 6, for example up to 4 carbon atoms as above. The aryl group may be as defined above, and may be substituted or unsubstituted. For example $R_5$ may be benzyl or phenethyl.

If X represents a heteroaromatic group then it may contain one, two or three heteroatoms selected from nitrogen, oxygen and sulphur. The heteroaromatic group may be unsubstituted or substituted as defined above for an aryl group, and may for example be a pyrrole, indole, isoindole, pyrazole, imidazole, pyridine, quinoline, isoquinoline, pyridazine, pyrimidine, pyrazine, furan, isoxazole oxazole or thiophene. In particular X may be a pyrrole, indole, pyridine, quinoline, isoquinoline or furan.

Particularly preferred salts of the compounds of the present invention are pharmaceutically acceptable addition salts such as hydrochlorides.

Particularly preferred compounds of formula I include:

(1a) 3'-deamino-3'-(2-benzoyl-4-morpholinyl)doxorubicin ($R_1$=OCH$_3$, $R_2$=$R_3$=OH, $R_4$=H, $R_5$=COC$_6$H$_5$), and its hydrochloride, and (1b) 3'-deamino-3'-(2-hydroxy-4-morpholinyl)doxorubicin ($R_1$=OCH$_3$, $R_2$=$R_3$=OH, $R_4$=H, $R_5$=H).

The compounds of formula 1 may be prepared by the formation of a substituted morpholinyl ring at C-3' on the sugar moiety of the anthracyclines through a reductive alkylation, based on using a dialdehyde of the general formula 2,

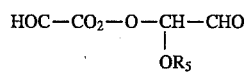

wherein $R_5$ has the same meaning as above reported with the proviso that $R_5$ does not represent hydrogen.

The compounds of formula 1 in which $R_5$ is hydrogen may be prepared by hydrolysis of the corresponding acyloxy derivatives.

Accordingly, the present invention provides a process for the preparation of an anthracycline glycoside of formula 1 as above defined or a pharmaceutically acceptable salt thereof, which process comprises (i) reacting an anthracycline of general formula 3,

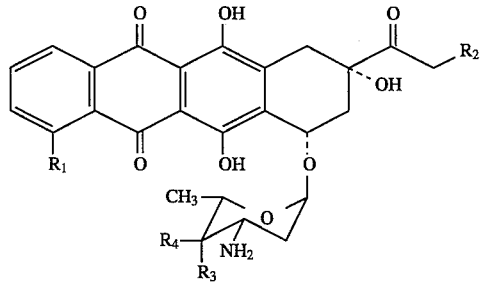

wherein $R_1$, $R_2$, $R_3$ and $R_4$ have the same meaning as above defined, or a salt thereof, with an aldehyde of formula 2 in the presence of a reducing agent such as an alkali metal cyanoborohydride and, if desired, converting the compound of formula 1 thus obtained into a pharmaceutically acceptable salt or;

(ii) deacylating a compound of formula 1 wherein $R_5$ represents an acyl group —COX as defined above, or a salt thereof, to provide a corresponding compound of formula 1 wherein $R_5$ represents hydrogen and, if desired, converting the compound of formula 1 thus obtained into a pharmaceutically acceptable salt thereof.

As examples of the starting anthracyclines of general formula 3 there may be given: doxorubicin (3a: $R_1$=OCH$_3$, $R_2$=$R_3$=OH, $R_4$=H), 4'-epidoxorubicin (3b: $R_1$=OCH$_3$, $R_2$=$R_4$=OH, $R_3$=H), daunorubicin (3c: $R_1$=OCH$_3$, $R_2$=$R_4$=H, $R_3$=OH) and 4-demethoxy-daunorubicin (3d: $R_1$=$R_2$=$R_4$=H , $R_3$=OH). These may be prepared as described by F. Arcamone in "DOXORUBICIN" Medicinal Chemistry, Vol.17, Academic Press, INC. (London) 1981. Other compounds of formula 3 may be prepared by analogous methods.

The reductive alkylation is typically carried using an excess of the dialdehyde 2. The reductive alkylation is generally carried out in a mixed aqueous polar organic medium, such as water-acetonitrile, generally at pH of about 6.5 in the presence of an alkali metal cyanoborohydride e.g. sodium or potassium cyanoborohydride. The reaction can be usually completed in two hours at room temperature. The desired product is isolated from the reaction mixture by solvent extraction and purified by column chromatography and may be obtained as its hydrochloride by treatment with methanolic hydrogen chloride. A dialdehyde of formula 2 is prepared via a Malaprade reaction on the 1-acyl derivative of a sugar, prepared as described in J. Org. Chem., 28 2999 (1963) and having general formula 2'.

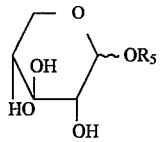

wherein $R_5$ has the same meaning above reported with the proviso that $R_5$ does not represent hydrogen atom.

In order to prepare derivatives of formula 1 in which $R_5$ represents hydrogen atom, the acyloxy residue of acyloxy derivatives of formula 1 may be removed by using an equivalent amount of metal alkoxy such as sodium methylate in dry organic polar solvent such as methanol. The product thus obtained may be extracted with methylene chloride from the reaction mixture (previously adjusted to pH 5 with aqueous hydrogen chloride), the organic solvent concentrated to small volume, and the desired product isolated as its hydrochloride by treating with methanolic hydrogen chloride.

As a further aspect, the invention provides pharmaceutical compositions comprising an anthracycline glycoside of formula 1 or a pharmaceutically acceptable salt thereof in combination with a pharmaceutically acceptable diluent or carrier. Conventional carriers and diluents may be used. The compositions may be formulated and administered in conventional manner.

The compounds of the invention are useful in methods of treatment of the human and animal body by therapy. They are useful as anti-tumour agents in the treatment of certain mammalian tumours. A therapeutically effective amount is administered to a patient having a tumour to ameliorate or improve the condition of the patient. An amount sufficient to inhibit the growth of the tumour may be administered.

The following Examples illustrate the invention.

EXAMPLE 1

Preparation of 1-benzoyl-2,2'-oxydiacetaldehyde
(2a: $R_5$=COC$_6$H$_5$)

1-O-benzoyl-β-L-arabinopyranoside (2a': $R_5$=COC$_6$H$_5$) (0.8 g, 3.14 mmole), prepared as described in J. Org. Chem., 28 2999 (1963), was dissolved in water (50 ml) and treated with sodium periodate (1.4 g, 6.3 mmole) at 0° C. for two hours. Barium chloride was added and the mixture was brought to pH 7 with sodium carbonate. The mixture was filtered, concentrated under reduced pressure and the title compound 2a was extracted with acetonitrile and used for the next step without further purification. TLC on Kieselgel Plate F$_{254}$ (Merck), eluting system methylene chloride/methanol (6/1 by volume) R$_f$=0.84.

EXAMPLE 2

Preparation of 3'-deamino-3'-(2-benzoyl-4-morpholinyl) doxorubicin (1a: $R_1$=OCH$_3$, $R_2$=$R_3$=OH, $R_4$=H, $R_5$=COC$_6$H$_5$)

To a solution of doxorubicin hydrochloride (3a, 0.3 g, 0.52 mmole) dissolved in a mixture of water (5 ml) and acetonitrile (13 ml) was added the solution of dialdehyde 2a prepared as described in Example 1. The pH was adjusted to 7.5 with triethylamine. After 15 minutes the pH was brought to 5.5 and the stirred mixture was treated with sodium cyanoborohydride (15 mg) dissolved in water (1 ml). After seven minutes the mixture was worked up by dilution with water and extraction with methylene chloride. The organic phase was concentrated to small volume and purified on silicic acid column using as eluting system a mixture of methylene chloride/methanol (97/3 by volume) to give the title compound 1a (0.15 g) as hydrochloride upon treatment with methanolic anhydrous hydrogen chloride. TLC on Kieselgel Plate F$_{254}$ (Merck), eluting system methylene chloride/methanol (10/1 by volume) Rf=0.63. FD–MS: m/z=733. $^1$HNMR (200 MHz, CDCl$_3$) δ: 1.36 (d, J=6.5 Hz, 3H, 5'-CH$_3$); 1.80 (m, 2H, 2'-CH$_2$); 2.16 (dd, J=4.1, 14.7 Hz, 8-Hax); 2.37 (dd, J=1.0, 14.7 Hz, 1H, 8-Heg); 2.4–2.7 (m, 4H, 3'-H, NCH$_2$CH$_2$O, NCH(H)CH—O); 2.8–3.1 (m, 1H, NCH(H)—CH—O); 3.04 (d, J=19.0 Hz, 1H, 10-Hax); 3.28 (dd, J=1.0, 19.0 Hz, 1H, 10-Heg); 3.68 (m, 1H, 4'-H); 3.7–4.1 (m, 3H, 5'-H, NCH$_2$CH$_2$O); 4.07 (s, 3H, 4-OCH$_3$; 4.68 (s, 1H, 9-OH); 4.74 (m, 2H, CH$_2$OH); 5.30 (m, 1H, 7-H); 5.57 (m, 1H, 1'-H); 6.19 (m, 1H, NCH$_2$—CH—O); 7.4–8.0 (m, 8H, Ph, 1-H, 2-H, 3-H); 13.26 (s,1H 11-OH); 13.98 (s, 1H, 6-OH).

EXAMPLE 3

Preparation of 3'-deamino-3'-(2-hydroxy-4-morpholinyl)-doxorubicin
(1b: $R_1$—OCH$_3$, $R_2$=$R_3$=OH, $R_4$=H, $R_5$=H)

Compound 1a (0.1 g, 0.13 mmole), prepared as described in Example 1, was dissolved in methanol (5 ml ) and treated with sodium methylate (10 mg). After 10 minutes the reaction mixture was brought to pH 5 with aqueous hydrogen chloride, diluted with water and extracted with methylene chloride. The organic phase was concentrated to small volume and treated with methanolic anhydrous hydrogen chloride to give the title compound 1b in the form of hydrochloride. TLC on Kieselgel Plate F$_{254}$ (Merck), eluting system methylene chloride/methanol (10:1 by volume) R$_f$=0.2.

TABLE 2

| Antitumor activity against P388/DX (Johnson) Leukemias. | | |
|---|---|---|
| | P388/DX[1] | |
| Compound | Dose[2] (mg/kg) | T/C[3] % |
| 1a | 1.2 | 175 |
| Doxorubicin | 13–16.9 | 86–100 |

[1]10$^5$ cells/mouse (P388/DX, Johnson) transplanted i.v. in CDF1 mice. Treatment on day 1 after inoculation of tumor.
[2]Optimal Dose
[3]Median survival time; % over treated controls.

Biological Assay

3'-deamino-3'[2-benzoyl-4-morpholinyl]doxorubicin (1a) was tested "in vitro" against LoVo and LoVo-resistant-doxorubicin (LoVo/DX) cells using a single cell plating technique after 4 hr treatment (Colony assay). The 50% inhibition concentration ($IC_{50}$) was calculated using concentration-response curves. Compound 1a was tested in comparison with Doxorubicin. Data are reported in Table 1.

TABLE 1

| | Cytotoxicity after 4 hr treatment $IC_{50}$ = ng/ml[1] | | |
|---|---|---|---|
| Compound | LoVo $IC_{50}$(ng/ml) | LoVo/DX $IC_{50}$(ng/ml) | R.I.[2] |
| 1a | 6.9 | 27 | 3.9 |
| Doxorubicin | 60 | 2160 | 36 |

[1]$IC_{50}$ = concentration inhibiting 50% colony growth
[2]R.I. = Resistance Index = ($IC_{50}$ LoVo/DX)/($IC_{50}$LoVo)

Compound 1a was evaluated "in vivo" against P388 murine Leukemias resistant to Doxorubicin, in comparison with Doxorubicin. Data are reported in Table 2.

We claim:

1. An anthracycline glycoside of formula 1:

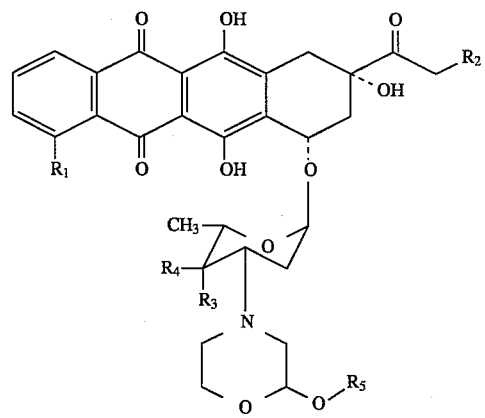

wherein $R_1$ is a methoxy group; $R_2$ is hydroxy; $R_3$ is hydroxy; $R_4$ represents hydrogen; $R_5$ represents an acyl residue —COX in which is X is a phenyl group; or a pharmaceutically acceptable salt thereof.

2. A compound according to claim 1 which is 3'-deamino-3'-(2-benzoyl-4-morpholinyl)doxorubicin or its hydrochloride.

* * * * *